United States Patent
Fallis et al.

(10) Patent No.: US 10,261,021 B2
(45) Date of Patent: Apr. 16, 2019

(54) METHOD AND DEVICE FOR DETECTING ALKYLATING AGENTS

(75) Inventors: Ian Fallis, South Glamorgan (GB); Ian Morgan, South Glamorgan (GB)

(73) Assignee: UNIVERSITY COLLEGE CARDIFF CONSULTANTS LIMITED, Cardiff (GB)

( * ) Notice: Subject to any disclaimer, the term of this patent is extended or adjusted under 35 U.S.C. 154(b) by 370 days.

(21) Appl. No.: 13/879,866

(22) PCT Filed: Oct. 17, 2011

(86) PCT No.: PCT/GB2011/052004
§ 371 (c)(1),
(2), (4) Date: Apr. 17, 2013

(87) PCT Pub. No.: WO2012/052747
PCT Pub. Date: Apr. 26, 2012

(65) Prior Publication Data
US 2013/0224876 A1    Aug. 29, 2013

(30) Foreign Application Priority Data

Oct. 18, 2010 (GB) .................................. 1017553.7

(51) Int. Cl.
*G01N 21/78* (2006.01)
*G01N 31/22* (2006.01)

(52) U.S. Cl.
CPC ............. *G01N 21/78* (2013.01); *G01N 31/22* (2013.01)

(58) Field of Classification Search
None
See application file for complete search history.

(56) References Cited

U.S. PATENT DOCUMENTS

| 4,132,527 A | 1/1979 | Maekawa et al. |
| 5,935,862 A | 8/1999 | Novak |

FOREIGN PATENT DOCUMENTS

| DE | 3914801 | 11/1990 | |
| DE | 100 35 199 | 1/2002 | |
| EP | 0 147 660 | 7/1985 | |
| WO | 98/53883 | 12/1998 | |
| WO | 2004/081561 | 9/2004 | |
| WO | WO 2004/081561 | * 9/2004 | ............. G01N 31/22 |
| WO | 2007/074461 | 7/2007 | |
| WO | 2012/052747 | 4/2012 | |

OTHER PUBLICATIONS

Menger, F.M., et al. Rapid Deactivation of Mustard via Microemulsion Technology, 1990, Journal of American Chemical Society, vol. 112, pp. 8201-8203.*

(Continued)

*Primary Examiner* — Xiaoyun R Xu
(74) *Attorney, Agent, or Firm* — Jackson Walker LLP

(57) ABSTRACT

A method is provided for detecting alkylating agents, the method comprising bringing together a first solvent, one or more surfactants, a base, a reagent comprising a nucleophilic nitrogen atom, and a suspected alkylating agent. A device suitable for putting said method into effect is also provided.

13 Claims, 4 Drawing Sheets

(56) References Cited

OTHER PUBLICATIONS

Menger, F. M. et al., Rapid Deactivation of Mustard via Microemulsion Technology, 1990, Journal of American Chemical Society, vol. 112(22), pp. 8201-8203.*
Holmberg, K. et al. Organic Synthesis in Microemulsions: An Alternative or a Complement to Phase Transfer Catalysis, 2003, by Marcel Dekker, Inc.*
Intellectual Property Office (Great Britain); Great Britain Application No. 1017553.7; Search Report; dated Jan. 27, 2011.
European Patent Office; PCT Application No. PCT/GB2011/052004; International Search Report; dated Apr. 24, 2012.
Agree, A. M., et al; Quantitative Determination of Micro and Semi-Micro Concentrations of Acylating Agents by 4-(p-Nitrobenzyl)Pyridine Reagent; Talanta, vol. 13, 1151-1160; 1966.
Bender, D. F., et al; Spectrophotometric Determination of Alkylating Agents with 4-Picoline and o-Dinitrobenzene; Analyst, vol. 90; 630-634; Jan. 1, 1965.
Brewer, J. H., et al; Biological-Chemical Indicator for Ethylene Oxide Sterilization; Journal of Pharmaceutical Sciences; vol. 55, No. 1, Jan. 1966.
Cox, P. J., et al; The Effect of Plasma on the Reaction of Cyclophosphamide with 4-(p-Nitrobenzyl)-Pyridine; Chem-Biol. Interactions; vol. 10, 103-114, 1975.
Dacre, J. C., et al; Toxicology and Pharmacology of the Chemical Warfare Agent Sulfur Mustard; Pharmacological Reviews; vol. 48, No. 2, 1996.
De, T. K., et al; Solution Behaviour of Aerosol OT in Non-Polar Solvents; Adv. Colloid Interface Sci., vol. 59, 95-193, 1995.
Epstein, J., et al; Use of y-(4-Nitrobenzyl)pyridine as Analytical Reagent for Ethylenimines and Alkylating Agents; Analytical Chemistry; vol. 27, No. 9, Sep. 1955.
Fallas, I A., et al; Locus-Specific Microemulsion Catalysts for Sulfur Mustard (HD) Chemical Warfare Agent Decontamination; J. Am. Chem. Soc. 2009, vol. 131, No. 28, 9746-9755; 2009.
Fischer, G.W.; Zur Reaktion von Phosphorsaurealkylestern mit 4-(4-Nitrobenzyl)-pydrin (NBP); Journal f. prakt. Chemie. Band 315, Heft 5, 901-908, 1973 (partial English translation attached).
Gilman, A., et al; The Biological Actions and Therapeutic Applications of the B-Chloroethyl Amines and Sulfides; vol. 103, No. 2675; 409-415, Apr. 5, 1946.
Kales, S. N., et al; Acute Chemical Emergencies; The New England Journal of Medicine; vol. 350, No. 8, 800-808, Feb. 19, 2004.
Kawazoe, Y., et al; Studies on Chemical Carcinogens. A Simple Method for Characterization of the Alkylating Ability of Compounds of using 4-(p-Nitrobenzyl)pyridine; Chem. Phara. Bull., vol. 30, No. 6, 2077-2086, 1982.
Menger, F. M., et al; Rapid Deactivation of Mustard via Microemulsion Technology; J. Am. Chem. Soc., vol. 112, No. 22, 8201-8203, 1990.
Menger, F.M., et al; Organic Reactivity in Microemulsion Systems; J. Am. Chem. Soc., vol. 113, No. 25, 9621-9624, 1991.
Muller, G., et al; Selektive Photometrische Bestimmung Aliphatischer Nitroolefine mit Hilfe des Alkylierungsindikators; 4-(4-Nitrobenzyl)pyridin (NBP); Int. Arch. Occupational and Environmental Health; vol. 36, 299-301, 1976.
Norpoth K., et al; Thin-Layer Chromatography of 4-(4'-Nitrobenzyl)-pyridine-reactive compounds in Tobacco Smoke; Hygiene-Institut, University of Munster, Germany, May 21, 1970.
Norpoth, K., et al; Quantitative Determination of Alkylating Cytostatics on TLC plate with 4-pyridinecarboxaldehyde-2-benzothiazolylhydrazone; Arzneimittel-Forschung, vol. 23, No. 11, 1973.
Noweir, M. H., et al; An Improved Method for Determination of Phosgene in Air; American Industrial Hygiene Association Journal; Mar. 1971.
Preussmann, R., et al; Identification of Different Classes of Alkylating Agents by a Modification of the Color Reaction with 4-(4-Nitrobenzyl)-pyridine (NBP); Arzneimittel-Forschung, vol. 19, 1969.
Rink, R., et al; Primary Structure and Catalytic Mechanism of the Epoxide Hydrolase from Agrobacterium Radiobacter AD1; The Journal of Biological Chemistry; vol. 272, No. 23, 14650-14657, Jun. 6, 1997.
Sano, A, et al.; 4-Acetylpyridine 2-Benzothiazolylhydrazone AS, A Chromogenic Reagent for Common Epoxides; Analytical Letters, 18(A10), 1221-1229, 1985.
Sawicki, E., et al; Five New Methods for the Spectrophotometric Determination of Alkylating Agents including Some Extremely Sensitive Autocatalytic Methods; Analytical Chemistry, vol. 35, No. 10, Sep. 1963.
Stedman, R. L.; The Chemical Composition of Tobacco and Tobacco Smoke; United States Department of Agriculture, Oct. 18, 1967.
Takitani, S., et al; Spectrodensitometric Determination of Trichothecene Mycotoxins with 4-(p-Nitrobenzyl)pyridine on Silica Gel Thin-Layer Chromatograms; Journal of Chromatography, vol. 172, 335-342, 1979.
Turner, C. R.; Spectrophotometric Determination of Organophosphorus Pesticides with 4-(4-Nitrobenzyl)pyridine; Analyst, vol. 99, 431-434, 1974.
Wagner, G. W., et al; Molybdate/Peroxide Oxidation of Mustard in Microemulsions; Langmuir, vol. 17, 4809-4811, 2001.
Wilson, R. E., et al; The Accleration of the Hydrolysis of Mustard Gas by Alkaline Colloidal Solutions; Massachusetts Institute of Technology, No. 57, Aug. 8, 1922.
Wilson, R. E., et al; The Solubility and Specific Rates of Hydrolysis of Mustard Gas in Water; Massachusetts Institute of Technology, No. 58, Sep. 15, 1922.
Yang, Y. Y., et al; Kinetics and Mechanism of the Hydrolysis of 2-Chloroethyl Sulfides; J. Org. Chem., vol. 53, 3293-3297, 1988.
Zocher, F., et al; A Colorimetric Assay suitable for screening Expoxide Hydrolase Activity; Analytica Chimica Acta 391, 345-351, 1999.
Mackay, "Reactivity and Formulation in Microemulsions", L'Actualité chimique, 1991, pp. 161-167, Société chimique de France, Paris, France.
Mackay et al., "Phase behavior and QLS in potassium linoleate/n-alkanol microemulsions", J. Dispersion Science and Technology, 1985, vol. 6, No. 2, pp. 193-207.
Murray et al., "Coordination Chemistry of Thioethers, Selenoethers, and Telluroethers in Transition-Metal Complexes", Chem. Rev. 1981, vol. 81, pp. 365-414.
Bera et al., "Microemulsions: a novel approach to enhanced oil recovery: a review", J Petrol Explor Prod Technol, 2015, pp. 255-268, vol. 5.
Binks, "Relationship between Microemulsion Phase Behavior and Macroemulsion Type in Systems Containing Nonionic Surfactant", Langmuir, 1993, pp. 25-28, vol. 9, No. 1.
Epstein et al., "Use of γ-(4=Ritrobenzyl)pyridine as Analytical Reagent for Ethylenimines and Alkylating Agents", Analytical Chemistry, Sep. 1955, pp. 1435-1439, vol. 27, No. 9.
Hloucha, "Microemulsions", Ullmann;s Encyclopedia of Industrial Chemistry Academy, 2015, pp. 1-4.
John et al., "Phase Behavior and Properties of a Microemulsion in the Presence of NaCl", Langmuir, 1994, pp. 2084-2087, vol. 10, No. 7.
Mathew et al., "Role of alcohols in the formation of inverse microemulsions and back extraction of proteins/enzymes in a reverse micellar system", Separation and Purification Technology, 2007, pp. 199-215, vol. 53.
Ruckenstein, "Microemulsions, Macroemulsions, and the Bancroft Rule", Langmuir, 1996, pp. 6351-6353, vol. 12, No. 26.
Watarai, "Review: Microemulsions in separation sciences", Journal of Chromatography, 1997, pp. 93-102, vol. 780.
Winsor, "Hydrotropy, Solubilisation and Related Emulsification Processes, Part I", Trans. Faraday Soc., 1947, pp. 376-398, vol. 44.
Winsor, "Hydrotropy, Solubilisation and Related Emulsification Processes, Part V", Trans. Faraday Soc., 1948, pp. 451-471, vol. 44.
"Brancroft rule"—Wikipedia dated Sep. 3, 2017.
Fallis, et al., Supporting Information for "Locus Specific Microemulsion Catalysts for Sulfur Mustard (HD) Chemical Warfare Agent Decontamination", J. Am. Chem. Soc., 2009, vol. 131, No. 28, pp. 9746-9755; Supplemental pp. S1-S25.

(56) References Cited

OTHER PUBLICATIONS

Groenewold, et al., "Detection of 2-Chloroethyl Ethyl Sulfide and Sulfonium Ion Degradation Products on Environmental Surfaces Using Static SIMS", American Chemical Society—Environmental Science & Technology, 1995, 29, retrieved on Aug. 29, 2018, pp. 2107-2111.

Destro, et al., "X-ray Structures and Anionotropic Rearrangements of Di-tert-butyl-Substituted Thiiranium and Thiirenium Ions. A structure-Reactivity Relationship", American Chemical Society—J. Org. Chem., Published on Web May 11, 2000, retrieved Aug. 29, 2018, pp. 3367-3370.

Destro, et al., "Detection and kinetics of the single-crystal to single-crystal complete transformation of a thiiranium ion into thietanium ion", www.rsc.org/pccp—Physical Chemistry Chemical Physics, Jun. 15, 2009, retrieved on Aug. 29, 2018, pp. 7181-7188.

Reed, Christopher A., "Accounts of Chemical Research—H+, CH3+, and R3Si+ Carbonate Reagents: When Triflates Fail", Center for s and p Block Chemistry, Department of Chemistry, University of California, Riverside, California 92521, received on May 29, 2009, downloaded on Aug. 29, 2018, pp. 121-128.

Lin, et al., "Thiourea-catalysed ring opening of episulfonium ions with indole derivatives by means of stabilizing non-covalent interactions", Nature Chemistry, published online Sep. 16, 2012, pp. 817-824.

\* cited by examiner

METHOD AND DEVICE FOR DETECTING ALKYLATING AGENTS

The present invention relates to a method and device for detecting alkylating agents, particularly (but not exclusively) potentially harmful alkylating agents, such as bis(2-chloroethyl) sulphide (often known as "sulphur mustard" or HD) and 2-chloro-N-(2-chloroethyl)-N-methyl-ethanamine (known as HN2 and one of the compounds known as "nitrogen mustards").

Many alkylating agents are toxic and have been used as chemical warfare agents (CWAs) for many years. Sulphur mustard and nitrogen mustard are two potent vesicants which have been used as CWAs. Whilst such compounds are no longer legally used on the battlefield, such compounds may be found on a regular basis throughout the world (mainly because of inadequate disposal methods) and potentially from belligerent groups or states. Furthermore, certain nitrogen mustards have possible legitimate uses as chemotherapeutic agents. There is therefore a need to provide methods and devices for detecting such chemicals so that adequate security and safety measures may be put in place when such a chemical is found. Many methods and devices exist for the in-field detection of such compounds. Some of the known methods require the use of one or more of expensive instrumentation, mains-voltage electrical power supply or specialist training. Some detection methods suffer from false positives and hence lack specificity.

A known method for detecting alkylating agents was developed by Epstein et al. The suspected alkylating agent is added to 4-nitrobenzyl pyridine (often known to those skilled in the art as 4-NBP or merely NBP) and is heated. It is believed the alkylating agent and 4-NPB form a cationic salt. Base, usually in the form of a hydroxide ion source, is then added which causes the formation of an intensely coloured dye (the formation of the dye indicating the presence of an alkylating agent). This known method requires the analyte and 4-NBP to be heated in order to form the salt. Furthermore, this method requires the sequential addition of the analyte and base because the base reacts with 4-NBP itself (obviously such a competitive reaction is undesirable).

The method and device of the present invention seek to address one or more of the problems mentioned above.

In accordance with a first aspect of the present invention, there is provided a method for detecting alkylating agents, the method comprising:
bringing together a first solvent, one or more surfactants, base, a reagent comprising a nucleophilic nitrogen atom, and a suspected alkylating agent.

The method of the present invention facilitates the detection of an alkylating agent without having to use a two-step process of (i) heating the alkylating agent and reagent, and (ii) subsequently adding a base as is used in the Epstein based methods. In detecting an alkylating agent, the reagent comprising a nucleophilic nitrogen atom typically reacts with an alkylating agent to form a species, the presence of which may be detectable.

Whilst not wishing to be restricted by theory, it is believed that the method of the present invention may operate by forming a micelle-containing solution. The one or more surfactants may form micelles in the first solvent, particularly if the first solvent is aqueous.

The method may therefore comprise providing a micelle-containing solution comprising the first solvent and one or more surfactants, and bringing together the micelle-containing solution, the suspected alkylating agent, the reagent comprising a nucleophilic nitrogen atom and the base. The micelle-containing solution may comprise the first solvent and the one or more surfactants.

The term "micelle-containing solution" refers to a fluid dispersion of micelles in the first solvent. Those skilled in the art will be familiar with the term "micelle". The micelles may have a mean largest dimension of less than about 50 nm, optionally from 10 to 30 nm, optionally from 10 to 20 nm, optionally from 3 to 50 nm, optionally less than 20 nm and optionally from 3 to 20 nm.

Whilst not wishing to be restricted by theory, it is believed that the reagent comprising the nucleophilic nitrogen atom is typically located within the micelles (the interior of the micelles being occupied by the hydrophobic, oleophilic "tail" groups of the surfactant molecules), and is therefore isolated from any species located in the continuous, typically aqueous, phase of the micelle-containing solution with which the reagent may react (such as OH species).

The method of the present invention optionally comprises bringing together the first solvent, a second solvent which is substantially immiscible with the first solvent, one or more surfactants, the base, the reagent comprising a nucleophilic nitrogen atom, and a suspected alkylating agent, wherein the reagent comprising a nucleophilic nitrogen atom is soluble in the second solvent.

Whilst not wishing to be restricted by theory, it is believed that the addition of the second solvent may facilitate the operation of the method of the present invention by forming a microemulsion.

The method may therefore comprise providing a microemulsion comprising the first solvent, the second solvent and one or more surfactants, and bringing together the microemulsion, the suspected alkylating agent, the reagent comprising a nucleophilic nitrogen atom and the base. The microemulsion may comprise the first solvent, the second solvent and the one or more surfactants.

The term "microemulsion" refers to a fluid dispersion of two immiscible liquids and one or more surfactants. If a microemulsion is formed, the droplets in the microemulsion may have a mean largest dimension of less than about 100 nm, optionally from 10 to 100 nm, optionally from 20 to 50 nm, optionally from 3 to 100 nm, optionally from 3 to 50 nm, optionally less than 20 nm and optionally from 3 to 20 nm.

Macroscopically, a microemulsion appears as an optically clear fluid because the scattering of visible light is very low. Microemulsions form spontaneously (without the shear often required to generate macroemulsions) and are thermodynamically stable.

Whilst not wishing to be restricted by theory, it is understood that the reagent is typically located in the droplets of the microemulsion, and therefore is isolated from any species located in the continuous phase of the microemulsion with which the reagent may react (such as OH species).

Whilst not wishing to be restricted by theory, it is believed that, if the first solvent is aqueous and the second solvent is a solvent which is immiscible with water (typically an organic solvent, and typically what may be known to those skilled in the art as an oil or oleophilic solvent), the reagent (which may, for example, be a pyridine-based compound which is soluble in such organic solvents) preferentially dissolves in the second solvent (as opposed to the first solvent), and is located within the droplets of the microemulsion, separated from the base with which the reagent may otherwise react or be decomposed by. The base would be generally associated with the aqueous solvent. The reagent comprising a nucleophilic nitrogen atom may therefore be susceptible to reaction with (or decomposition by) a base.

Those skilled in the art will realise that the method may comprise providing a macroemulsion comprising the first solvent, the second solvent and one or more surfactants, and bringing together the macroemulsion, the suspected alkylating agent, the reagent comprising a nucleophilic nitrogen atom and the base. If a macroemulsion is formed, the droplets in the macroemulsion may have a mean largest dimension of greater than about 100 nm, preferably greater than about 500 nm and further more preferably from 500 to 1000 nm.

Reaction of the reagent and an alkylating agent (and subsequent reaction of the product with base) may lead to formation of a coloured compound, formation of a coloured compound being indicative of the presence of the alkylating agent. The method of the present invention may therefore comprise sensing for the presence of colouration. The colouration may be associated with the formation of a nitrogen-containing conjugated compound, such as a dihydropyridine (such as is the case where the reagent is 4-NBP). The colouration is preferably blue.

The method may comprise sensing the speed of formation of colouration, the speed of formation of colouration being indicative of the reactivity of the alkylating agent. Sensing the speed of formation may be performed qualitatively (for example, by observation with the human eye) or quantitatively (for example, by measurement using a spectrometer or the like).

The method may comprise sensing the intensity of colouration, the intensity of colouration being indicative of the concentration of the alkylating agent. Sensing the intensity of colouration may be performed qualitatively (for example, by observation with the human eye) or quantitatively (for example, by measurement using a spectrometer or the like).

The method may comprise sensing for a change in colouration, and adding further base dependent on the change in colouration. For example, the method may comprise sensing for a change (typically a decrease) in intensity of colouration and adding base dependent on the change in intensity of colouration. It has been found that in certain circumstances, reaction of the analyte produces acid, and if a large amount of analyte is present, the pH drops significantly so that no further reaction takes place. Addition of further base causes an increase in pH, which facilitates the reaction of the analyte and said reagent, thereby generating an increase in colouration.

The first solvent may be aqueous; this is optionally preferred for the formation of a micelle-containing solution, a microemulsion or a macroemulsion. The first solvent may comprise water and one or more co-solvents. It is preferred that the first solvent is water.

The second solvent, if present, is optionally immiscible with water. The second solvent is preferably an organic solvent. Examples of such solvents will be well known to those skilled in the art, but may be, for example, aromatic solvents (such as toluene and benzene), cyclic alkanes (such as cyclopentane and cyclohexane) and acyclic alkanes (such as pentane, hexane, heptane and octane), substituted variants thereof (such as dichloromethane and trichloromethane), and aliphatic or aromatic esters.

The nucleophilic nitrogen atom may be provided by an unsaturated cyclic moiety, such as an azolyl or pyridinyl moiety. The said moiety may comprise one or more substituents, either in, or attached to, the ring. For example, the azolyl moiety may be a thiazolyl or imidazolyl moiety. It is preferred that the nucleophilic nitrogen atom is provided by a pyridinyl moiety.

The one or more surfactants may be cationic, anionic or non-ionic surfactants. The preferred nature of the one or more surfactants typically depends, amongst other things, on the particular alkylating agent to be detected. Anionic surfactants have proved to be particularly effective in detecting sulphur mustards, sulphur half mustards and nitrogen mustards. Microemulsions formed from cationic or non-ionic surfactants may not be so effective for those chemical warfare agents, but certain cationic and non-ionic surfactants form microemulsions which are effective for the detection of other alkylating agents.

Examples of cationic surfactants which may be used in the method of the present invention are cetyl trimethylammonium bromide (CTAB) and other alkyltrimethylammonium salts, cetylpyridinium chloride (CPC), polyethoxylated tallow amine (POEA), benzalkonium chloride (BAC), benzethonium chloride (BZT) and dodecyl thrimethylammonium chloride (DTAC).

Examples of anionic surfactants which may be used in the method of the present invention are perfluorooctanoate (PFOA or PFO), perfluorooctanesulfonate (PFOS), sodium dodecyl sulfate (SDS) (otherwise known as sodium lauryl sulfate and also known as sodium lauryl ether sulfate (SLES)), alkyl benzene sulfonate salts, alkyl sulfonate salts, dialkyl succinyl sulphonate (AOT) salts and fatty acid salts.

Examples of non-ionic surfactants which may be used in the method of the present invention are alkyl poly(ethylene oxide), polysorbates (such as those based on Polyoxyethylene Glycol, including the Tween series (ex.Tween 20, Tween 80), the Brij (R) series, the [[ex.Triton detergent[Triton]] series (ex.Triton X-100), alkylphenol poly(ethylene oxide), copolymers of poly(ethylene oxide) and poly(propylene oxide) (commercially called poloxamers or poloxamines), alkyl polyglucosides, including octyl glucoside, decyl maltoside and fatty alcohols, such as cetyl alcohol and oleyl alcohol, cocamide MEA, cocamide DEA and dodecyl dimethylamine oxide.

The one or more additional components may comprise a co-surfactant. The co-surfactant may comprise one or more alcohols, such as an alcohol having up to 12 carbon atoms, for example, one or more of methanol, ethanol, propanol, butanol, pentanol, hexanol and heptanol. Co-surfactants can also be 1,2 or 1,3 dihydroxy alkanes and glycol monoethers (e.g. 2-butoxy-ethan-1-ol). The co-surfactant may form part of the micelles (if a micelle-containing solution is used in the method of the present invention).

The preferred nature of the one or more surfactants may typically depend, amongst other things, on the reagent comprising a nucleophilic nitrogen atom. For example, 4-nitrobenzyl pyridine is stable in anionic microemulsions, but is not stable in non-anionic or cationic microemulsions.

A microemulsion, if formed, may be formed with the second solvent being located within droplets and the first solvent being located outside of droplets. As indicated above, it is preferred that the microemulsion formed is an oil-in-water type microemulsion. Therefore, it is preferred that the amount of first solvent is greater than the amount of second solvent. Under certain circumstances, it may be desirable to have an inverse microemulsion (i.e. water-in-oil), in which case it is preferred that the amount of second solvent is greater than the amount of first solvent.

The first solvent, the second solvent (if present), the one or more surfactants, the reagent comprising a nucleophilic nitrogen atom and suspected alkylating agent may optionally be brought together at a pH of at least 9, optionally at least 11, further optionally at least 12, optionally up to 14, optionally from 12 to 14 and optionally from 13 to 14. The pH of the solution is increased by the addition of a concentrated hydroxide solution such as sodium hydroxide, potassium hydroxide or tetra(n-butylammonium) hydroxide.

The method may comprise providing a liquid comprising the one or more surfactants and the first solvent (and optionally the reagent, base, second solvent (if present) and the co-surfactant (if present)) and bringing together said liquid and the suspected alkylating agent.

For example, the suspected alkylating agent may be deposited onto a substrate (such as a piece of porous filter paper), and a liquid comprising the one or more surfactants, the first solvent, the second solvent (if present), the reagent and base may be deposited onto the filter paper in the same place where the suspected alkylating agent was deposited.

It may be desirable to keep said reagent and the one or more surfactants apart until shortly before the method is performed, because some surfactants (such as sodium dodecyl sulfate) are weak alkylating agents which react with said reagent over a prolonged period of time. Many surfactants (e.g. alkyl benzene sulfonates) do not present such problems.

Said liquid may optionally be substantially devoid of one or both of the base and reagent, in which case the method may comprise bringing together said liquid, the suspected alkylating agent and that or those of the base and reagent which are not present in the liquid mixture. This is because a liquid comprising the base and reagent may have a limited shelf life (typically less than about three months, although certain surfactant-reagent combinations have longer shelflifes), because of a suspected reaction between the reagent and the base or between the reagent and certain surfactants. It is especially preferred if the liquid mixture is substantially devoid of the reagent. In this case, one or both of the base and reagent may be provided on a substrate (for example, by loading a filter paper with a solution of the reagent and then removing the solvent). The suspected alkylating agent may be deposited onto the substrate and then the liquid deposited onto the substrate. Those skilled in the art will realise that the liquid may be deposited onto the substrate prior to the suspected alkylating agent.

The liquid may be delivered by any suitable means. For example, the liquid may be delivered as a spray.

The suspected alkylating agent may be collected using any suitable method known to those skilled in the art. For example, pure sulphur mustard is a viscous liquid at ambient temperature and so may be collected using a swab, a scraping device or pipette.

The method may comprise providing a substrate for the receipt of the suspected alkylating agent. The substrate is preferably absorbent; such a substrate typically retains the suspected alkylating agent in one place (reducing the likelihood of unwanted accidental spillage or loss of suspected alkylating agent) and presents a large surface area for exposure to other reagents. The substrate may be provided with one or both of the reagent and base. A liquid as described above may be added to the substrate.

The liquid may be provided in a reservoir which forms part of a testing device. The device may be provided with a frangible barrier which is breakable to permit said liquid to leave the reservoir.

The testing device may be provided with a collection surface for the collection of suspected alkylating agent. The collection surface may be provided by a swab, for example. The testing device may be arranged so that the frangible barrier is breakable to permit liquid to leave the reservoir and contact the collection surface. It is preferred that the liquid is movable from the reservoir to the collection surface by gravity. For instance, the reservoir may be located directly above the collection surface when the frangible barrier is broken.

The collection surface may be provided with the reagent.

A flow path may be provided between the reservoir and the collection surface. The flow path may be provided by a guide for the liquid. The guide may be in the form of a conduit (wherein the liquid travels along the inside of the conduit). Alternatively, the guide may comprise one or more external surfaces for the receipt of liquid, the external surface forming a flow path to the collection surface (typically through the interaction of the liquid with the one or more external surfaces). One or both of the base and reagent may be provided in the flow path. Liquid travelling from the reservoir, along said flow path contacts said one or both of the base and reagent before contacting the collection surface.

The testing device may comprise a filter. The filter may be downstream of the collection surface. The filter may be provided with base (for example, the filter may comprise a basic ion exchange resin, such as Amberlyst(R) A-26 {OH}).

The testing device may comprise a sampler portion and a containment portion, the sampler portion being removable from, and replaceable into, the containment portion, wherein the sampler portion comprises the collection portion and reservoir. The sampler portion may also comprise the guide for the liquid (if present).

The containment portion typically provides a receptacle which, when the device is used, collects any liquid formerly present in the reservoir and the suspected alkylating agent.

In accordance with a second aspect of the present invention, there is provided a method for detecting alkylating agents, the method comprising:

Bringing together a microemulsion or a micelle-containing solution, a suspected alkylating agent, a base and a reagent comprising a nucleophilic nitrogen atom, the microemulsion or micelle-containing solution comprising a first solvent and one or more surfactants, the microemulsion (if present) comprising a second solvent which is substantially immiscible with the first solvent.

The first solvent, second solvent (if present), the one or more surfactants and the reagent may comprise those features described above in relation to the method of the first aspect of the present invention. The microemulsion or micelle-containing solution may have those features described above in relation to the method of the first aspect of the present invention.

The reagent is typically soluble in the second solvent or in a micelle-containing solution.

One or both of the reagent and base may be provided in the microemulsion or in a micelle-containing solution. Alternatively, one or both of the reagent and base may be provided separately from the microemulsion or from the micelle-containing solution. For example, the method may comprise providing a substrate, the substrate being provided with one or both of the reagent and base.

The method of the present invention may comprise those features described above in relation to the method of the first aspect of the present invention. For example, the method may comprise providing a testing device as described above in relation to the method of the first aspect of the present invention.

In accordance with a third aspect of the present invention, there is provided a kit for detecting alkylating agents, the kit comprising a substrate for the receipt of a suspected alkylating agent and a liquid, the liquid comprising one or more surfactants and a first solvent,
one or both of the substrate and liquid comprising a reagent comprising a nucleophilic nitrogen atom.

The liquid may comprise a second solvent which is substantially immiscible with the first solvent, said reagent being soluble in the second solvent.

The liquid may comprise those features described above with reference to the method of the first aspect of the present invention.

For example, the liquid optionally comprises a microemulsion or micelle-containing solution. The microemulsion or micelle-containing solution may have the properties as described above in relation to the method of the first aspect of the present invention. The second solvent, if present, may be entrapped within the droplets of a microemulsion, with the first solvent forming the continuous phase external to the droplets or the first solvent may be entrapped within the droplets of the microemulsion, with the second solvent, if present, forming the continuous phase external to the droplets. The second solvent, if present, may optionally be entrapped within the droplets, and the second solvent is optionally an organic solvent which is substantially immiscible with water, and the first solvent is optionally water or an aqueous solvent.

The kit may further be provided with a base. The base may be provided on the substrate or in the liquid. Optionally, none or only one of the reagent and the base is provided in the liquid.

In accordance with a fourth aspect of the present invention, there is provided a device for detecting alkylating agents, the device comprising:
A reservoir holding a liquid comprising one or more surfactants and a first solvent;
A reagent comprising a nucleophilic nitrogen atom;
A collection surface for the collection of a suspected alkylating agent; and
A frangible barrier which is breakable to permit said liquid to leave the reservoir,
the collection surface being so located relative to the reservoir that liquid leaving the reservoir contacts the collection surface.

The liquid may comprise a second solvent which is substantially immiscible with the first solvent, the reagent being soluble in the second solvent.

In detecting an alkylating agent, the reagent comprising a nucleophilic nitrogen atom typically reacts with an alkylating agent to form a species, the presence of which may be detectable. For example, the species may be coloured, and therefore the formation of the colour associated with the species is indicative of the presence of an alkylating agent.

The device is so configured that liquid is movable from the reservoir to the collection surface by gravity. For instance, the reservoir may be located directly above the collection surface when the frangible barrier is broken.

Alternatively a solution of the reagent comprising first solvent, co-surfactant, surfactant and second solvent (if present) may be sprayed onto the collection surface. This solution may contain base.

The collection surface may be provided with the reagent.
The device may be provided with base.
The first solvent, the second solvent (if present), the one or more surfactants, the base, the co-surfactant (if present) and the reagent comprising the nucleophilic nitrogen may comprise those features described above in relation to the method of the first aspect of the present invention.

The liquid may comprise those features described above with reference to the method of the first aspect of the present invention.

A flow path may be provided between the reservoir and the collection surface. The flow path may be provided by a guide for the liquid. The guide may be in the form of a conduit (wherein the liquid travels along the inside of the conduit). Alternatively, the guide may comprise one or more external surfaces for the receipt of liquid, the external surface forming a flow path to the collection surface (typically through the interaction of the liquid with the one or more external surfaces). One or both of the base and reagent may be provided in the flow path. Liquid travelling from the reservoir, along said flow path contacts said one or both of the base and reagent before contacting the collection surface.

The device may comprise a filter. The filter may be downstream of the collection surface. The filter may be provided with base (for example, the filter may comprise a basic ion exchange resin, such as Amberlyst(R) A-26 {OH}).

The device may comprise a sampler portion and a containment portion, the sampler portion being removable from, and replaceable into, the containment portion, wherein the sampler portion comprises the collection portion and reservoir. The sampler portion may also comprise the guide for the liquid (if present).

The containment portion typically provides a receptacle which, when the device is used, collects any liquid formerly present in the reservoir and the suspected alkylating agent.

In accordance with a fifth aspect of the present invention, there is provided a device for detecting alkylating agents, the device comprising a porous substrate comprising a first region provided with one of a base and a reagent comprising a nucleophilic nitrogen atom, a second region provided with the other of the base and said reagent and a sample receiving region for the receipt of a sample of suspected alkylating agent, the device being operable to receive an eluting liquid for carrying base or reagent from the first region into the second region such that an admixture of the suspected alkylating agent, the reagent and the base is formed.

The substrate may optionally be provided with a gap region substantially free of both base and reagent, the gap region being located between the first region and the second region. The physical separation of reagent and base facilitates the detection of alkylating agent and improves shelf-life.

The sample receiving region optionally overlaps with the first region of the substrate.

The first region of the substrate is optionally provided with said reagent and the second region of the substrate is optionally provided with base.

The reagent may comprise those features described above in relation to the method of the first aspect of the present invention. For example, the reagent may be 4-NBP.

The substrate may comprise a cellulose, glass or polymer based support.

The device is optionally operable to produce a coloured response in the presence of an alkylating agent.

In accordance with a sixth aspect of the present invention, there is provided a method for detecting alkylating agents, the method comprising providing a device in accordance with the fifth aspect of the present invention and providing an eluting solvent which causes the one of the base and reagent present in the first region of the substrate to move to the second region of the substrate.

The eluting solvent is optionally a polar solvent. The eluting solvent may comprise water and/or one or more alcohols.

In accordance with a seventh aspect of the present invention, there is provided a liquid for the detecting of alkylating agents, the liquid comprising a first solvent, one or more surfactants, and a reagent comprising a nucleophilic nitrogen atom.

The liquid may comprise a second solvent which is substantially immiscible with the first solvent, the reagent being soluble in the second solvent.

The liquid may further comprise a base.

The liquid may further comprise a co-surfactant.

The first solvent, the second solvent (if present), the one or more surfactants, the base, the co-surfactant (if present) and the reagent comprising the nucleophilic nitrogen may comprise those features described above in relation to the method of the first aspect of the present invention.

The liquid may comprise a microemulsion or micelle-containing solution. The microemulsion or micelle-containing solution may comprise those features described above in relation to the method of the first aspect of the present invention. The second solvent, if present, may be largely entrapped within the droplets of the microemulsion, with the first solvent forming the continuous phase external to the droplets or the first solvent may be largely entrapped within the droplets of the microemulsion, with the second solvent, if present, forming the continuous phase external to the droplets. In the case of a microemulsion, it is preferred that the second solvent is entrapped with the droplets, and it is further preferred that the second solvent is an organic solvent which is substantially immiscible with water, and that the first solvent is water or an aqueous solvent.

The liquid of the present invention may be provided by, for example, a liquid comprising the first solvent, the second solvent and the one or more surfactants (but excluding the reagent) to a substrate which is provided with the reagent.

The present invention will now be described by way of example only with reference to the following figures of which:

Figure 1:
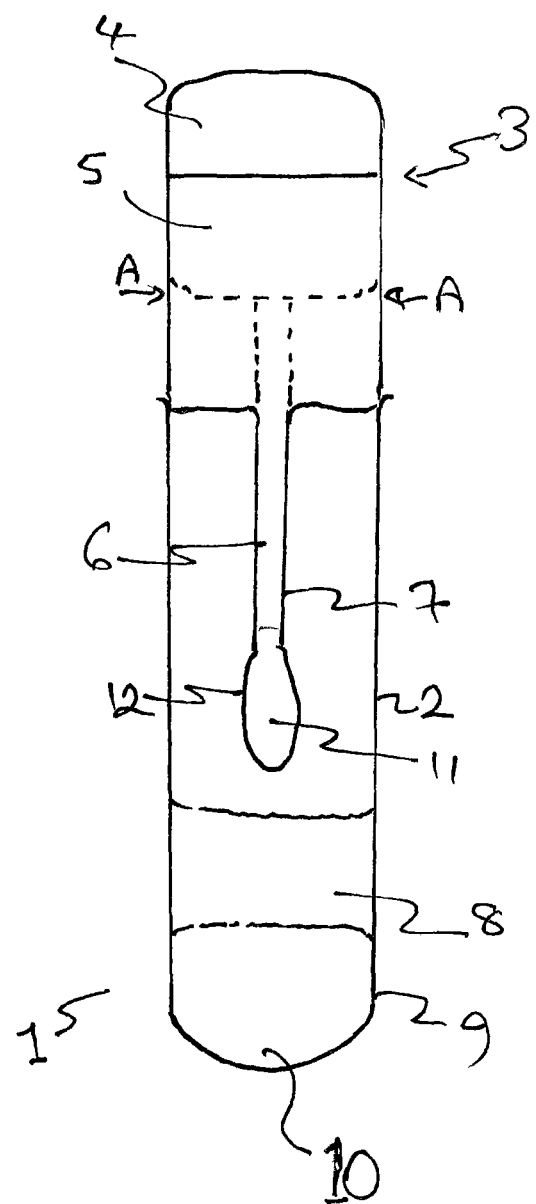
FIG. 1 is a schematic side-on view of an example of an embodiment of a device in accordance with the present invention.

The method of the present invention was investigated by making various different microemulsions and adding various alkylating agent to those microemulsions.

Anionic, cationic and non-ionic oil-in-water microemulsions were made by mixing water, an organic solvent (toluene or a mixture of toluene and heptane), a surfactant and a co-surfactant (n-butanol) as summarised in representative examples below. All surfactants, solvents and reagents were purchased from Sigma-Aldrich Ltd and were used as received. Materials of standard or technical grades were used on all occasions. Surfactant solutions and microemulsions were formulated using distilled water.

Anionic 1.01 g SDS (sodium dodecyl sulphate), 0.48 g toluene, 0.91 g n-butanol and 7.66 g water were mixed to form a microemulsion.

Cationic 1.0 g DTAC (dodecyltrimethylammonium chloride), 1.0 g toluene, 1.0 g n-butanol and 7.0 g water were mixed to form a microemulsion.

Non-ionic 1.0 g Brij 56, 0.5 g toluene, 1 g n-butanol and 7.5 g water were mixed to form a microemulsion.

Inverse Anionic Microemulsion

An inverse i.e. water-in-oil anionic microemulsion was formed using the general method of De and Maitra (Adv. Colloid Interface Sci., 1995, vol. 59, pages 95-193). The microemulsion comprised water, n-butanol, toluene/heptanes and sodium dioctyl sulfosuccinate (often known as AOT).

Once a microemulsion had been formed, the reagent (4-NBP) was added to the microemulsion. The pH of the microemulsion was then adjusted to 12-13 by slow addition of tetrabutylammonium hydroxide. The final reagent loading of the microemulsion was 1 wt %.

1 ml of the microemulsion was then mixed at ambient temperature with 10 μL of suspected alkylating agent. The intensity of colouration and the speed with which any colouration formed was monitored in the two minute period after mixing of the suspected alkylating agent and the microemulsion. The results of these investigations are shown in Table 1.

Those skilled in the art will realise that many of the alkylating agents used in these experiments are dangerous and are regulated by the Geneva Protocol of 1925 and the Chemical Weapons Convention of 1993. The development, production and stockpiling of some of these alkylating agents (in particular, sulphur mustard, half sulphur mustard and nitrogen mustard) is prohibited.

TABLE 1

| | | Microemulsion | | | |
|---|---|---|---|---|---|
| | Analyte | Anionic | Anionic (inverse) | Cationic | Non-ionic |
| 1 | HD (sulfur mustard) | Very rapid(intense purple) | — | — | — |
| 2 | CEES (half sulfur mustard) | Very rapid, (intense purple) | No change | Slow (pale purple) | Slow (pale purple) |
| 3 | NH2 (nitrogen mustard) | Rapid, (intense purple) | | Very slow(feint purple) | Very slow (feint purple) |
| 4 | Methyl iodide | Very slow (pale purple) | | Moderate (strong purple) | Moderate (strong purple) |
| 5 | Benzyl bromide | Moderate, (intense purple) | | Rapid, (intense purple) | Rapid, (intense purple) |
| 6 | Benzyl chloride | Slow (very pale purple) | | No change | No change |
| 7 | Allyl bromide | Moderate (pale purple) | | Moderate (strong purple) | Moderate (strong purple) |
| 8 | Epichlorohydrin | Rapid (intense purple) | | Moderate (strong purple) | Moderate (strong purple) |
| 9 | Epibromohydrin | Rapid (intense purple) | | Moderate (strong purple) | Moderate (strong purple) |

TABLE 1-continued

| | Microemulsion | | | |
|---|---|---|---|---|
| Analyte | Anionic | Anionic (inverse) | Cationic | Non-ionic |
| 10 1,2-epoxypropane | Rapid (intense purple) | | Rapid (strong purple) | No change |
| 11 1,2-epoxyoctane | Very slow (pale purple) | | Slow (very pale purple) | No change |

It can be seen from Table 1 that anionic microemulsions are particularly effective for the detection of the chemical warfare agents sulphur mustard, half sulphur mustard and nitrogen mustard. The cationic and non-ionic microemulsions are not so effective for those chemical warfare agents, but the cationic and non-ionic microemulsions are effective for the detection of other alkylating agents. The inverse (i.e. water in oil) anionic microemulsions proved to be generally ineffective.

Observation of the speed of formation, and intensity, of colouration may provide a qualitative identification of the analyte in question, for a given amount of analyte. For example, for the anionic microemulsion, the speed of formation of colouration for different alkylating agents is given below:

sulfur mustards (HD)>>nitrogen mustard (HN)>benzylic/allylic bromides>epihalohydrins (Cl, Br, I)>benzylic/allylic chlorides>alkyl iodides, alkyl esters of sulphonic acids, dialkylesters of sulphuric acid>epoxides>alkyl bromides>alkyl chlorides Without wishing to be bound by theory, the applicant believes that the effective performance of the anionic microemulsion towards sulphur mustard (HD) may be explained as follows with reference to Reaction Scheme 1. The anionic interfacial region is believed to protect the reagent 1 contained within the droplets from attack from base located in the aqueous phase. It is believed that the sulphur mustard forms positively charged episulfonium ions in the interface region, those positive ions having a tendency to collect in the anionic Stern layer. It is postulated that the ring strained episulfonium ion reacts with the reagent (in this case, 4-NBP) to produce a surface active cation $[R-(1)]^+$ which will localise at the interface of a droplet, where it will be exposed to base dissolved in the continuous aqueous phase. Base will cause deprotonation of the $[R-(1)]^+$ cation, thus forming the intensely blue coloured 4-(4-nitrobenzylidene)-1,4-dihydro-1-alkylpyridine dye 2.

Reaction Scheme 1

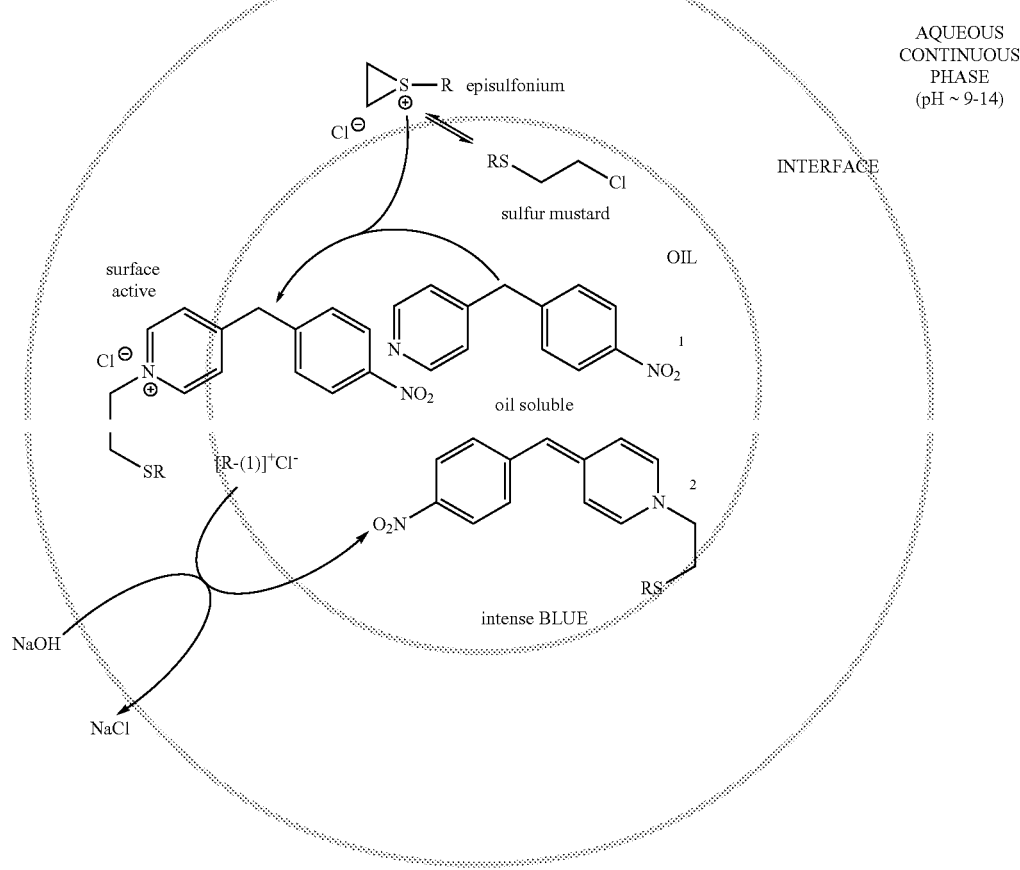

The effect of the structure of the reagent on detection performance was investigated. Compound 10 (an isomer of 4-NBP (compound 1)) gave similar (but slower) responses than compound 1, suggesting that the reaction of the reagent with the analyte is the rate determining step. Hydrazones 8, 9 were prepared (being more nucleophilic than compounds 1 and 10), but were found to be ineffective. Hydrazones 4, 7 were found to be ineffective in anionic microemulsions, but effective in cationic microemulsions, giving an intense green positive response.

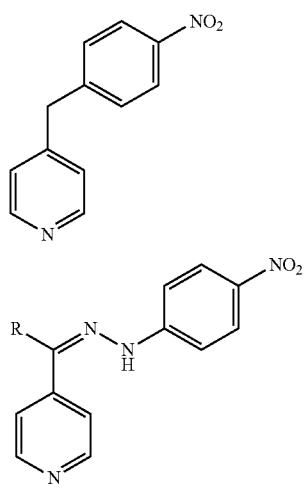

2 R = H
3 R = CH₃
4 R = Ph

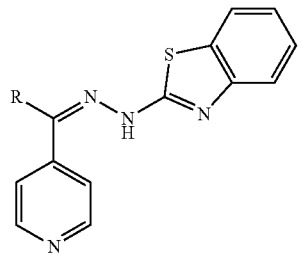

5 R = H
6 R = CH₃
7 R = Ph

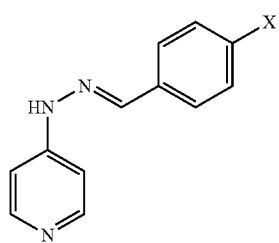

8 R = H
9 R = NO₂

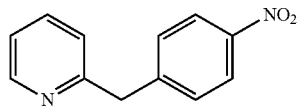

10

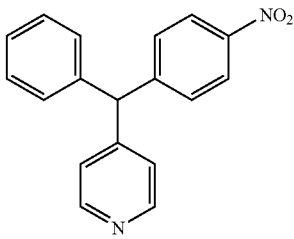

11

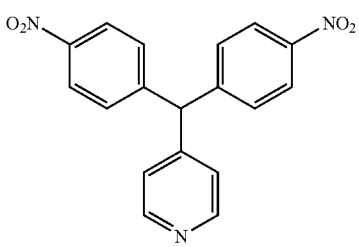

12

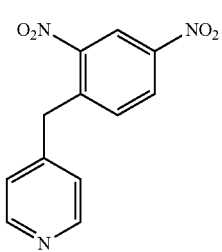

13

Figure 4:
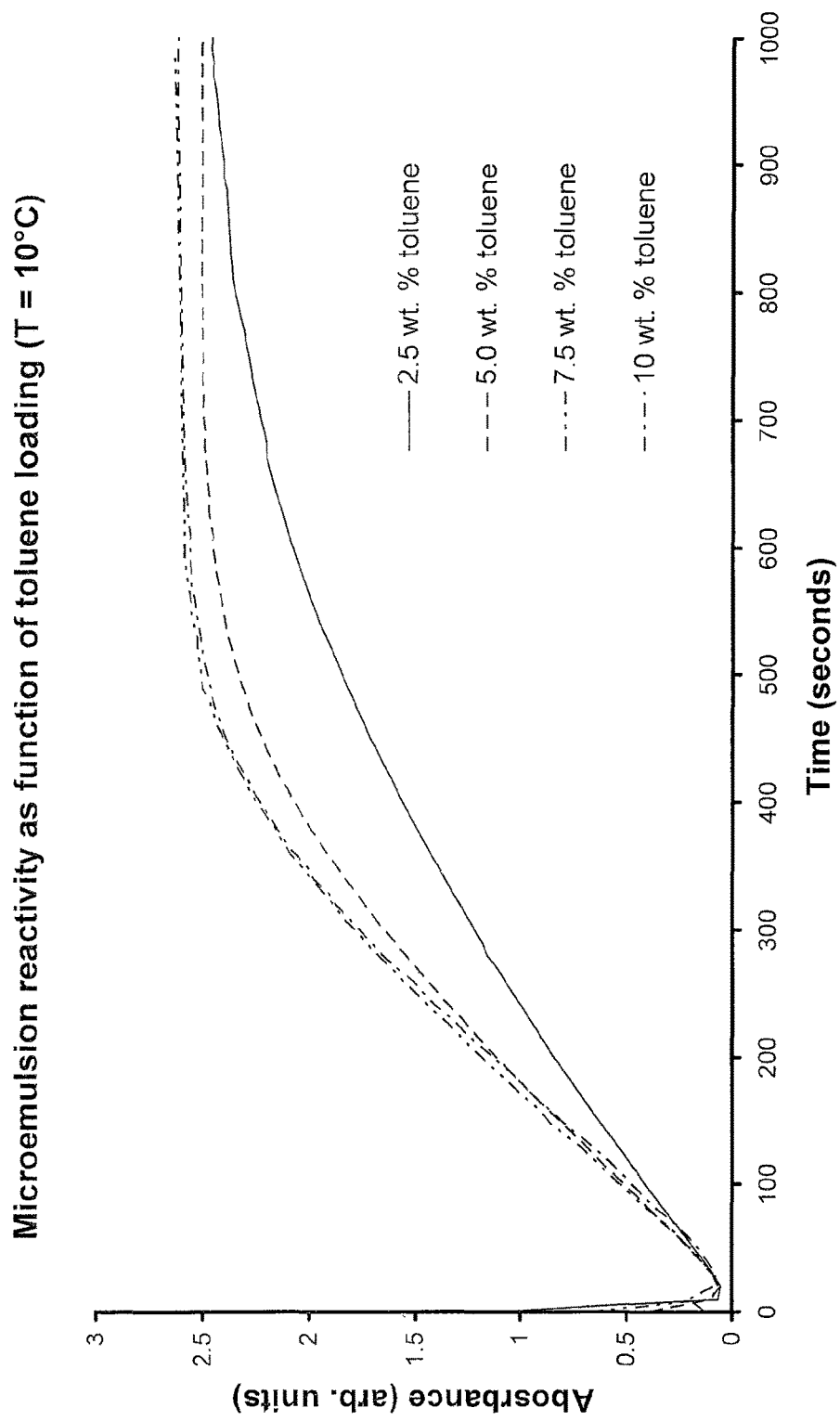
FIG. 4 shows the colour response against time of several different detecting liquids as a function of the amount of toluene (acting as a second solvent).

The effect of the amount of second solvent on the rate of detection was investigated. A solution consisting of 1.01 g SDS (sodium dodecyl sulphate), 0.91 g n-butanol and 7.66 g water was prepared and the amount of second solvent (in this case, toluene) was varied. FIG. 4 shows the absorbance at 565 nm as measured using spectrometer as a function of time, as a function of the amount of toluene used. It can be seen that at low levels of toluene (2%) the rate of formation of the coloured product (indicative of the rate of reaction between the alkylating agent and said reagent) is lower than at higher levels of toluene (say, 7.5% and 10%).

The surfactants used in the above microemulsions (anionic, cationic, non-ionic) may also be used to prepare micelle-containing solutions in which the second (water-immiscible) solvent is absent. The preparation of micelle-containing solutions is well-known to those skilled in the art (see, for example, "Surfactants and Interfacial Phenomena"—Milton J. Rosen, Wiley-Blackwell, (2004)-ISBN-10: 0471478180 or "The Colloidal Domain Where Physics, Chemistry and Biology Meet (Advances in Interfacial Engineering)"—D. Fennell Evans, Hakan Wennerstrom, Wiley-Blackwell, (1999)—ISBN-10: 0471242470). The speed of reaction in general is increased in the presence of the second solvent. Hence, microemulsions tend to produce more rapid reactions than the micelle-containing solutions. For example a system consisting of 1.01 g SDS (sodium dodecyl sulphate), 0.98 g of 2-butoxyethanol and 7.66 g water was prepared. This solution was found to be as effective as any toluene containing system.

EXAMPLE 1

FIG. 1 shows an embodiment of example of a device in accordance with the present invention. The device is denoted generally by reference numeral 1 and comprises a sampling portion 3 and a receptacle portion 2, the sampling portion 3 being removable out of, and into, the receptacle portion 2. The sampling portion 3 comprises a reservoir 4 in fluid communication with a conduit 7 which forms a flow path between the reservoir 4 and a swab 11. The reservoir 4 contains a liquid 5 comprising an anionic oil-in-water microemulsion or a solution of an anionic surfactant, the droplets or micelles containing 4-NBP and the aqueous continuous phase being at a pH of from 12-13. The swab 11 provides a sample collection surface denoted generally by reference numeral 12. In use, the sampler portion 3 is grasped by a user and the collection surface 12 brought into contact with a suspected alkylating agent. The sampling portion 3 is then reinserted into the receptacle portion 2. A frangible barrier (not shown) is provided between the reservoir 4 and the conduit 7. The application of pressure by the user at points A as shown in FIG. 1 causes the barrier to break, releasing the liquid 5 into the conduit 7 and thence onto swab 11 which is carrying the suspected alkylating agent. The liquid then washes into the observation region 10 at the bottom of the receptacle portion 2. The presence of alkylating agent is indicated by the liquid in the observation region being blue-purple.

A filter 8 is provided in the receptacle portion 2 to remove unwanted solids.

EXAMPLE 2

In an alternative device which is otherwise the same as that of Example 1, the swab 11 is impregnated with 4-NBP, the liquid 5 in the reservoir 4 being devoid of 4-NBP, and being at a pH of about 12-14. The separation of 4-NBP and base may extend the shelf-life of the device.

EXAMPLE 3

In an alternative device which is otherwise the same as that of Example 1, the conduit 7 is provided with solid 4-NBP and base, both supported on a solid substrate, the liquid 5 in the reservoir 4 being devoid of 4-NBP and base.

EXAMPLE 4

In an alternative device which is otherwise the same as that of Example 1, the conduit 7 is provided with solid 4-NBP supported on a solid substrate, the liquid 5 in the reservoir 4 being devoid of 4-NBP, at a pH of about 12-14.

EXAMPLE 5

In an alternative device which is otherwise the same as that of Example 1, the swab 11 is impregnated with solid 4-NBP, the liquid 5 in the reservoir 4 being devoid of 4-NBP and base. The filter 8 comprises a basic anion exchange resin (for example, Amberlyst (R) A-26 {OH}). Any alkylated NBP in the liquid passing through the resin is converted to the dye, the eluent appearing as a dark blue or purple liquid. In the absence of any alkylated NBP, the eluent is colourless. The resin itself turns purple in the presence of NBP or alkylated NBP, thereby providing an indication that NBP was present in the original liquid. This colouration of the filter may be used to indicate that the absence of any colouration in an eluent is due to the absence of an alkylating reagent in an analyte, not the NBP having decomposed or reacted to form an inactive species (for example, with base).

EXAMPLE 6

In an alternative device which is otherwise the same as that of Example 5, the swab 11 not being impregnated with solid 4-NBP, but rather the liquid 5 in the reservoir 4 being provided with 4-NBP.

EXAMPLE 7

Figure 2:
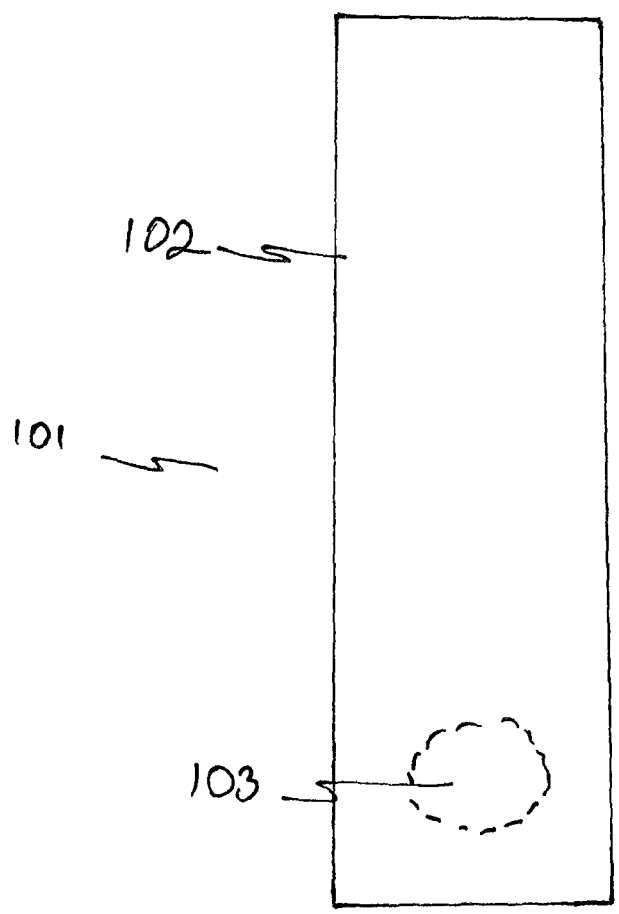
FIG. 2 is a schematic side-on view of a further example of an alternative embodiment of a device in accordance with the present invention.

FIG. 2 shows an embodiment of example of a device in accordance with the present invention. The device is denoted generally by reference numeral 101 and comprises a porous substrate 102 (typically a cellulose or polymer based support) comprising a sample receiving region 103. In use, a liquid sample of analyte is placed onto the sample receiving region. The liquid sample may be obtained, for example, by dipping the sample receiving region into liquid analyte or by using a sampling device (not shown) which is provided with a solvent e.g. a swab dipped in solvent, and passing the sampling device over a surface to be sampled. A liquid (not shown) may be placed onto the sample receiving region, the liquid comprising an anionic oil-in-water microemulsion or a micelle-containing solution, the droplets containing 4-NBP and the aqueous continuous phase being at a pH of from 12-13. The presence of an alkylating agent in the analyte will be indicated by the development of a blue-purple region where the analyte and liquid come into contact with one another.

EXAMPLE 8

In an alternative device which is otherwise the same as that of Example 7, the substrate 102 is impregnated with NBP, with the liquid being devoid of NBP.

EXAMPLE 9

In an alternative device which is otherwise the same as that of Example 7, the substrate 102 is impregnated with NBP and base, with the liquid being devoid of NBP and base.

EXAMPLE 10

In an alternative device which is otherwise the same as that of Example 7, the substrate is an anion exchange substrate which is impregnated with NBP, with the liquid being devoid of NBP and base.

EXAMPLE 11

Figure 3:
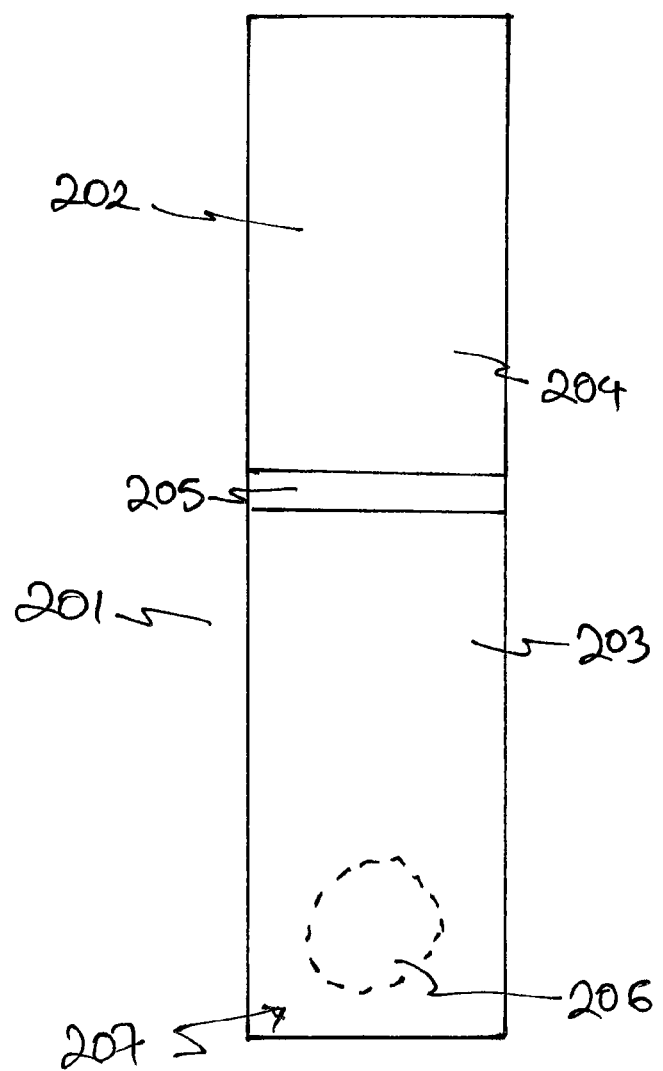
FIG. 3 is a schematic side-on view of yet a further example of an alternative embodiment of a device in accordance with the present invention.

FIG. 3 shows an embodiment of example of a device in accordance with the present invention. The device is denoted generally by reference numeral 201. The device 201 comprises a porous substrate 202 (such as a piece of filter paper, for example) comprising a first region 203 impregnated with NBP (but substantially devoid of base) and a second region 204 which is impregnated with base (but substantially devoid of NBP). A gap region 205 which is (prior to use of the device 201) devoid of both base and NBP is provided between the first 203 and second 204 regions. A sample receiving region 206 is provided, the sample receiving region overlapping with the first region 203.

In use, a sample of analyte is placed onto the sample receiving region (for example, using a sampling device [not shown] or by dabbing the device onto a sample [if the sample is liquid]). The end 207 of the device associated with the sample receiving region 206 is then inserted into a polar solvent (not shown, but a 50:50 vol:vol mixture of water and an alcohol). The polar solvent is drawn up the device, heading from end 207 towards second region 204. Any alkylating agent present in the sample reacts with the NBP to form a salt. Reaction of the alkylating agent with the NBP is promoted by the highly polar nature of the solvent (the polar solvent assisting in the formation of an intermediate ion [such as the episulfonium ion in the case of sulphur mustard]) which reacts with the NBP. Upon elution into the second region 204, the alkylated NBP is deprotonated by the base in the second region 204, forming the deeply coloured dye, thereby indicating the presence of an alkylating agent.

EXAMPLE 12

A further example of an embodiment of a method in accordance with the present invention is now presented using the vesicant bis 2-chloroethyl sulphide (HD) as an analyte. The vesicant was absorbed onto a cotton swab and a detection composition dropped onto the swab. Any colour change was observed and noted. The effect of the order of mixing of the various reaction components was investigated as is described below.

Composition 1 comprises 1 ml of a combination of sodium dodecylsulfate (10. wt %), 2-butoxyethanol (9 wt. %) and water (81 wt. %).

Composition 2 comprises 0.15 mL of tetrabutyl ammonium hydroxide solution (8 wt. % aqueous solution)

Composition 3 comprises 0.005 mL of a 4 wt. % solution of 4-nitrobenzyl pyridine in 2-butoxyethanol.

The following combinations of analyte and solutions were found to be effective:

A—Analyte, then Composition 1, then Composition 3, then Composition 2.
B. Composition 1, then Composition 3, then Composition 2 then analyte.
C. Composition 1, then Composition 2, then Composition 3 then analyte.
D. Analyte, then Composition 3, then Composition 1, then Composition 2.

A and D were found to be particularly effective.

EXAMPLE 13

A further example of an embodiment of a method in accordance with the present invention is now presented using the vesicant bis 2-chloroethyl sulphide (HD) as an analyte.

HD was added to 1 mL of a composition comprising dodecylbenzenesulfonic acid, sodium salt (5.1 g), 4-nitrobenzyl pyridine (79 mg), water (38 mL) and butoxyethanol (11 g), with vigorous shaking. A solution of 0.1 mL of sodium hydroxide solution (30 mg/1 mL in water) was then added. The presence of HD is indicated by a very pale yellow to intense blue-purple colour change. The speed and magnitude of response is proportional to the quantity of analyte provided that the pH of the remains above about 11. If there is a large amount of analyte, the pH may drop below about 11 due to production of acid as the analyte reacts. If the pH drops below about 11, then the colouration fades. Addition of suitable amounts of base restores the colour response.

EXAMPLE 14

The ability of 4-nitrobenzyl pyridine (4-NPB) in an anionic microemulsion to detect different alkylating agents was investigated using the general methodology described above in relation to Example 12, method C. 4-NBP was effective at detecting 2-chloroethyl ethyl sulphide, 2-chloro-N-(2-chloroethyl)-N-methyl-ethanamine, tris(2-chloroethyl) amine and benzyl bromide. 4-NBP was not effective at detecting methyl iodide.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims.

The invention claimed is:

1. A method for detecting a sulphur mustard chemical warfare agent, the method comprising:
    bringing together a first solvent, one or more surfactants, a base, a reagent comprising a nucleophilic nitrogen atom, and a suspected sulphur mustard chemical warfare agent,
    wherein the method comprises:
        providing a micelle-containing solution comprising the first solvent and one or more surfactants, or
        providing an oil-in-water microemulsion comprising the first solvent, wherein the first solvent is an aqueous solvent, one or more anionic surfactants and a non-aqueous second solvent in which the reagent comprising a nucleophilic nitrogen atom is soluble and which is substantially immiscible with the first solvent; and
        bringing together at a pH of at least 12 the microemulsion or the micelle-containing solution, the suspected sulphur mustard chemical warfare agent, the reagent comprising a nucleophilic nitrogen atom and the base, wherein the sulphur mustard chemical warfare agent forms an episulfonium ion which reacts with the reagent comprising a nucleophilic nitrogen atom.

2. The method according to claim 1 comprising sensing for the formation of colouration.

3. The method according to claim 2 comprising sensing the speed of formation of colouration, the speed of formation of colouration being indicative of the reactivity of the sulphur mustard chemical warfare agent.

4. The method according to claim 2 comprising sensing for a change in colouration, and adding further base dependent on the change in colouration.

5. The method according to claim 1 wherein the nucleophilic nitrogen is provided by an unsaturated cyclic moiety.

6. The method according to claim 4 wherein the nucleophilic nitrogen is provided by an azolyl or pyridinyl moiety.

7. The method according to claim 1 comprising providing a liquid comprising the microemulsion or micelle-containing solution and one of a base and the reagent comprising a nucleophilic nitrogen atom, and bringing together said liquid and the suspected sulphur mustard chemical warfare agent and the other of the base and reagent which is not present in the liquid.

8. The method according to claim 1 comprising providing a liquid comprising the microemulsion or micelle-containing solution, but being substantially devoid of base and the reagent, and bringing together said liquid, the suspected sulphur mustard chemical warfare agent, the base and the reagent comprising a nucleophilic nitrogen atom.

9. The method according to claim 7, wherein the suspected sulphur mustard chemical warfare agent and that or those of the base and reagent which are not present in the liquid are provided on a substrate.

10. The method according to claim 7 comprising providing a testing device comprising a reservoir wherein the liquid is provided in the reservoir.

11. The method according to claim 10 wherein the testing device is provided with a frangible barrier which is breakable to permit said liquid to leave the reservoir, the testing device is provided with a collection surface for the collection of suspected sulphur mustard chemical warfare agent and the testing device being arranged so that the frangible barrier is breakable to permit liquid to leave the reservoir and contact the collection surface, the liquid being movable from the reservoir to the collection surface by gravity.

12. The method according to claim 11 wherein a flow path is provided between the reservoir and the collection surface, the flow path being provided by a guide for the liquid, the guide being in the form of a conduit, wherein the liquid travels along the inside of the conduit, or the guide comprising one or more external surfaces for the receipt of liquid, the external surface forming a flow path to the collection surface.

13. The method according to claim 10, the testing device comprising a sampler portion and a containment portion, the sampler portion being removable from, and replaceable into, the containment portion, wherein the sampler portion comprises the collection portion and reservoir.

* * * * *

UNITED STATES PATENT AND TRADEMARK OFFICE
CERTIFICATE OF CORRECTION

PATENT NO. : 10,261,021 B2
APPLICATION NO. : 13/879866
DATED : April 16, 2019
INVENTOR(S) : Ian Fallis et al.

Page 1 of 1

It is certified that error appears in the above-identified patent and that said Letters Patent is hereby corrected as shown below:

In the Specification

1. In Column 2, Line 18, delete "OH" and insert -- $OH^-$ --, therefor.

2. In Column 2, Line 55, delete "OH" and insert -- $OH^-$ --, therefor.

3. In Column 14, Line 51, delete "Domain Where" and insert -- Domain: Where --, therefor.

Signed and Sealed this
Tenth Day of September, 2019

Andrei Iancu
*Director of the United States Patent and Trademark Office*